US005729620A

United States Patent [19]
Wang

[11] Patent Number: 5,729,620
[45] Date of Patent: Mar. 17, 1998

[54] COMPUTER-AIDED DIAGNOSIS SYSTEM AND METHOD

[76] Inventor: Shih-Ping Wang, 409 Becker La., Los Altos, Calif. 94022

[21] Appl. No.: 438,432

[22] Filed: May 10, 1995

Related U.S. Application Data

[63] Continuation-in-part of Ser. No. 129,255, Sep. 29, 1993, abandoned.

[51] Int. Cl.$^6$ ..................................................... G06K 9/00
[52] U.S. Cl. .................. 382/128; 382/132; 378/166
[58] Field of Search ................... 382/128, 132, 382/284; 364/413.13, 413.22; 378/37, 162–166

[56] References Cited

U.S. PATENT DOCUMENTS

| | | | |
|---|---|---|---|
| 4,499,491 | 2/1985 | Aron et al. | 358/102 |
| 4,737,921 | 4/1988 | Goldwasser et al. | 395/135 |
| 4,833,625 | 5/1989 | Fisher et al. | 395/139 |
| 4,839,807 | 6/1989 | Doi et al. | 364/413.13 |
| 4,841,555 | 6/1989 | Doi et al. | 378/98 H |
| 4,851,984 | 7/1989 | Doi et al. | 382/108 |
| 4,875,165 | 10/1989 | Fencil et al. | 364/413.22 |
| 4,907,156 | 3/1990 | Doi et al. | 364/413.13 |
| 4,908,876 | 3/1990 | DeForest et al. | 382/261 |
| 4,918,534 | 4/1990 | Lam et al. | 348/367 |
| 5,072,384 | 12/1991 | Doi et al. | 382/132 |
| 5,133,020 | 7/1992 | Giger et al. | 382/6 |
| 5,150,292 | 9/1992 | Hoffman et al. | 364/413.07 |
| 5,224,177 | 6/1993 | Doi et al. | 382/168 |
| 5,245,539 | 9/1993 | Romeas et al. | 382/132 |
| 5,331,550 | 7/1994 | Stafford et al. | 364/413.13 |
| 5,343,390 | 8/1994 | Doi et al. | 364/413.22 |

FOREIGN PATENT DOCUMENTS

| | | | |
|---|---|---|---|
| 2582819 | 12/1986 | France | G03B 21/00 |
| 3433141 | 3/1986 | Germany | G03B 42/02 |
| 3931531 | 4/1990 | Germany | A61B 5/00 |
| 2132353 | 5/1990 | Japan | G01N 23/18 |
| 9107135 | 5/1991 | WIPO | A61B 6/12 |

OTHER PUBLICATIONS

European Search Report dated Jan. 8, 1995.
Patent Abstracts of Japan, vol. 14, No. 360 (P–1088), Abstract of Japanese Publication No. 2132353.
Giger, et al., "An 'Intelligent' Workstation for Computer–aided Diagnosis," RadioGraphics, vol. 13, No. 3, May 1993, pp. 647–656.
Giger, et al., "Development of a 'smart' workstation for use in mammography," Proceedings of SPIE, vol. 1445, Image Processing, 1991, pp. 101–103.
Specht, D.F., "Probabilistic Neural Networks," Neural Networks, vol. 3, 1990, pp. 109–118.
Wu, Y., et al., "Computerized detection of clustered microcalcifications in digital mammograms: Applications of artificial neural networks," Med. Phys. 19(3), May/Jun. 1992, pp. 555–560.

(List continued on next page.)

*Primary Examiner*—Leo Boudreau
*Assistant Examiner*—Chris Kelly
*Attorney, Agent, or Firm*—Cooper & Dunham LLP

[57] ABSTRACT

X-ray images are displayed at both high-resolution and high illumination with annotation superimposed in registration therewith to point out suspected abnormalities identified through a process in which the x-ray images are digitized and the digitized information is subjected to feature extraction processing. For example, the x-ray images are displayed at both high-resolution and high illumination in the form of x-ray film images displayed on a light box while the annotation information is selectively superimposed on the same image by a separate imaging system co-acting with the light box. In this manner, the radiologist can view either the x-ray film alone, in the conventional manner, or the same x-ray film, at the same position and at the same high resolution and at the same or substantially the same illumination level but with annotation information superimposed and in registration therewith. In addition, alternative ways are disclosed for displaying the high resolution x-ray image and for selectively superimposing the annotation information thereon.

29 Claims, 4 Drawing Sheets

OTHER PUBLICATIONS

Wu, Y., et al., "Artificial Neural Networks in Mammography: Application to Decision Making in the Diagnosis of Breast Cancer," Radiology, vol. 187, No. 1, Apr. 1993, pp. 81–87.

Yoshimura, H., et al., "Development of a high quality film duplication system using a laser digitizer: Comparison with computed radiography," Med. Phys. 20(1), Jan./Feb. 1993, pp. 51–58.

Randall, T., "Varied Mammogram Readings Worry Researchers", Journal of the American Medical Association, vol. 269, No. 20, May 26, 1993, pp. 2616–2617.

Gonzales, R.C., et al. "Digital Image Processing," published by Addison–Wesley, Nov. 1987.

Russ, John C., "The Image Processing Handbook," CRC Press, Inc., 1992.

COMPUTER-AIDED DIAGNOSIS SYSTEM AND METHOD

REFERENCE TO RELATED APPLICATION

This application is a continuation-in-part of parent application Ser. No. 08/129,255 filed on Sep. 29, 1993 now abandoned, and hereby incorporates by reference the entire disclosure, drawings and claims of said parent application.

FIELD AND BACKGROUND OF THE INVENTION

This invention is in the field of x-ray technology and specifically relates to displaying x-ray images in a manner that is believed to assist in reading x-ray images. More specifically, the invention relates to displaying x-ray images together with annotation information derived by computer-aided analysis of the images. Still more specifically, the invention relates to a computer-aided diagnosis system and method for the detection of abnormalities from a digitized radiologic image and the production of a separate annotated map of the locations of the detected abnormalities for the purpose of annotating the radiologic image in a manner enabling the observer to view the film x-ray image, or an image of a comparable high resolution, together with the annotated map, without taking his or her eyes off the x-ray film and at an illumination level which is the same as or is comparable with that provided by a conventional light box. More specifically, the invention pertains to a computer-aided diagnosis system and method designed to improve diagnostic efficiency and accuracy by adding particularly convenient annotation to the original radiologic image.

The detection of abnormal anatomic regions in radiologic images using a computer system comprising of specialized software and possibly hardware components has been reported by, for example: Giger et al in May 1993 issue of RadioGraphics, pages 647–656; Giger et al in Proceedings of SPIE, Volume 1445 (1991), pages 101–103; Doi et al in U.S. Pat. No. 4,907,156; and Giger et al in U.S. Pat. No. 5,133,020. These and other references cited below in this patent specification are incorporated herein by reference as though fully set forth herein. These systems are generally referred to as Computer-Aided Diagnosis systems, or CAD systems, and are believed to be particularly useful to radiologists in the diagnostic process and particularly in screening radiologic procedures.

In a screening radiologic procedure, such as screening mammography, the patients typically are asymptomatic and true abnormalities (e.g., cancers) are believed to occur at a typical rate of about one case per one hundred patient examinations. Reading of the mammograms, when most of the mammograms are negative, can be a tedious task that can make it difficult to maintain a constantly high attention level. Some detectable abnormalities can be missed or misdiagnosed, which can result in delayed or more costly treatment, and can even result in a reduction of patient's chance of survival. According to an article in the May 26, 1993 issue of JAMA, pages 2616–2617, the misdiagnosis rate in mammograms is found to be in the range of 15 to 63%. The CAD system, serving as an electronic reminder or second reader, can assist radiologists in obtaining higher detection rate (higher sensitivity) for abnormalities or reducing the misdiagnosis rate (lowering the false-negative rate).

It is believed that a current procedure using a CAD system proceeds as follows. The radiologist views a radiologic image and reaches a preliminary diagnostic decision and then views a separate second image displayed on a CAD system. This second image has marked or annotated thereon the abnormalities that the CAD system detected. After reviewing the CAD-detected abnormalities, the radiologist then makes the final diagnostic decision, which may or may not be the same as the preliminary decision depending on whether additional diagnostic information was provided by the CAD system. Following the final diagnostic decision, and perhaps depending on the degree of suspicion for malignancy, the radiologist can recommend a course of further action, which can include no further action or further follow-up examinations or biopsy.

In the process of detecting abnormal anatomic features in radiologic images using a CAD system as described in the above cited references, the radiologic film image of a patient is processed through a film digitizer to generate a digitized image which is input as such into the system. The digitized image is then analyzed by a digital image processing computer with specialized software and perhaps hardware for abnormal anatomic feature detection. If abnormalities are detected, an annotated radiologic image is displayed on a special TV monitor, with markers placed around or adjacent the detected abnormalities. This TV monitor typically has a large dimension (typically a screen diagonal of 12 inches or larger) and a very high spatial resolution (typically more than 1000×1000 pixels). Because of the large dimension and high spatial resolution, this TV monitor typically is positioned at some distances away from the film. Typically the center of the monitor is significantly more than 12 inches from the center of the film on the conventional film illumination box. In addition, this TV monitor would have a low brightness (typically less than 100 foot-lamberts).

While the above described CAD system can point out the CAD-detected abnormalities to the radiologist, it is believed that the display method that it utilizes, using the high-resolution TV monitor, has certain shortcomings, such as, the process of using it is inconvenient and inefficient as is explained in more detail in the following. The high-resolution TV monitor is expensive, its spatial resolution is still much less than that of the original x-ray film, and its brightness and dynamic range are also very much inferior to those of an x-ray film viewed on a light box. Therefore, it is believed that a radiologist might not rely solely on the image displayed on the TV monitor to make diagnosis, but typically would repeatedly go back to the conventional film illumination box to view the original film image. This can lead to the loss of valuable time and can be uncomfortable at least because of the different brightness levels and spatial resolution levels of the two images. In addition, it is believed that diagnostic errors might arise from the need for the radiologist to shuttle back and forth between two different displayed images.

SUMMARY OF THE INVENTION

An object of the invention is to improve the display of combined x-ray images and CAD-detected abnormalities. A more specific object is to improve the convenience, accuracy and efficiency in the radiologist's viewing process by particularly effectively combining a high-brightness display of the original high quality film image with an annotation map registered therewith. Another objective is reduce the cost of equipment by using lower cost and widely available display components for certain displays. Yet another object of the invention is to provide annotation information that can include an alignment check or registration guide between the film image and the annotation information. Still another object of the invention is to provide a simple road map image on a small TV monitor located in close proximity to the film and containing a miniaturized annotation map superimposed on a miniaturized corresponding radiologic image of the same size and in registration therewith.

In an exemplary and non-limiting first embodiment of the invention, an inexpensive conventional film illumination light box is modified to house a back-projecting high intensity scanning light source, such as a scanning laser beam, which serves two functions: it uses the high intensity scanning light source to display an annotated map of the CAD-detected abnormalities and, at the same time, it uses the conventional fluorescent lamps in the conventional film illumination box to serve as a light box for a conventional film placed over its screen in registration with the displayed annotation map. The annotated map can be turned on or off independently by the radiologist with a on-off control, to provide the option of viewing the x-ray film alone or with the annotation map superimposed thereon. The annotation map can selectively provide additional information from the CAD system, such as the type of abnormalities and/or the probability or likelihood of the detected abnormalities. This additional information can be displayed as a part of the annotation map, e.g., by suitable variation in the shape, size, or brightness and/or duration of the displayed information identifying the CAD-detected abnormalities. Furthermore, the annotation map can selectively provide additional information from the CAD system as alignment check or guide, such as the breast outline in a mammogram or the torso outlines, lung or the heart borders in a chest film.

Because the high intensity scanning light source is used only to provide the annotation information and does not display the original x-ray film image, the spatial resolution requirement of this high intensity scanning light source can be reduced substantially. Because the film image and the annotation map are selectively displayed overlaid on each other, and in registration with each other, a radiologist can make a diagnosis by looking at only one displayed image, namely, the original image, with the locations of abnormalities marked or highlighted thereon by means of the superimposed annotation map.

In an exemplary and non-limiting second embodiment of the invention, an inexpensive conventional film illumination light box is made to function with an external front-projecting high intensity scanning light source, such as a scanning laser beam. The conventional film illumination light box is used in the traditional manner to illuminate the original film placed on the light box. The high intensity scanning light source is positioned externally to the light box and front-projects an annotated map of the CAD-detected abnormalities onto the original film and in registration with the film. As described in the first embodiment of the invention, the annotated map can be turned on or off independently by the radiologist with a on-off control, to provide the option of viewing the x-ray film alone or with the annotation map superimposed thereon. The annotation map can selectively provide additional information from the CAD system, such as the type of abnormalities and/or the probability or likelihood of the detected abnormalities. This additional information can be displayed as a part of the annotation map, e.g., by suitable variation in the shape, size, or brightness and/or duration of the displayed information identifying the CAD-detected abnormalities. Furthermore, the annotation map can selectively provide additional information from the CAD system as alignment check or guide, such as the breast outline in a mammogram or the torso outlines, lung or the heart borders in a chest film.

In an exemplary and non-limiting third embodiment of the inventory, the annotated information is presented as a simple annotated road map image on a small TV monitor, located in close proximity to the film being viewed at the light box. This small TV monitor displays a miniaturized annotation map superimposed on a miniaturized corresponding radiologic image of the same size as the map and in registration therewith. The center of the small TV monitor is typically less than 12 inches from the center of the film on the conventional film illumination box. In this manner, the radiologist still has to move his or her eyes back and forth between the original radiologic film image on the film illuminator and the annotated road map and, selectively, small version of the radiologic image displayed on a small TV monitor. While diagnostic errors might still arise from this back and forth movement, the much shorter distance and the much smaller angle subtended by the eye between the annotated road map and the original film image as compared to the system described by Giger et al, in Proceedings of SPIE, Volume 1445 (1991), pages 101–103, is expected be able to reduce the occurrence of such errors.

Stated in broader terms, in one aspect the invention is embodied in a system or a process providing digitized image data representing an x-ray image characterized by high spatial resolution, a processor which receives said digitized image data and generates as a function thereof an annotation map identifying image portions meeting selected criteria, and a display which displays said x-ray image, e.g., as a film image, for viewing at said high spatial resolution and at a high brightness level while selectively superposing thereon said annotation map in registration therewith.

In this context, the term high spatial resolution is used to mean a spatial resolution such as provided by x-ray film or such as provided by medical imaging devices which provide an image only in digital form such as, without limitation CT scanners or nuclear medicine cameras or MRI scanners or other scanners or other devices or systems. In some cases, identified as such in the specification and claims herein, the term high spatial resolution is used to mean spatial resolution at least at the level of that of x-ray film image. In still other cases, also identified as such, the term is used to mean spatial resolution comparable to that of x-ray film but higher than that of the typical currently known medical imaging systems that provide the primary image data only in digital form.

The term high brightness level is used herein to mean higher brightness level than provided by typical currently known display devices that have high spatial resolution, such as those used in the known process discussed above of using a high spatial resolution monitor to display a single, composed image that shows both a digitized version of an x-ray film and annotation markings for that film. In special cases identified as such, the term is used to mean brightness at the level of that provided be known illumination boxes (light boxes) used by radiologists. In still other cases identified as such, the term is used to mean brightness at levels such as provided by low spatial resolution (e.g., NTSC or PAL or SECAM spatial resolution or comparable or lower resolution) conventional TV monitors or computer terminal monitors.

DETAILED DESCRIPTION

Figure 1:
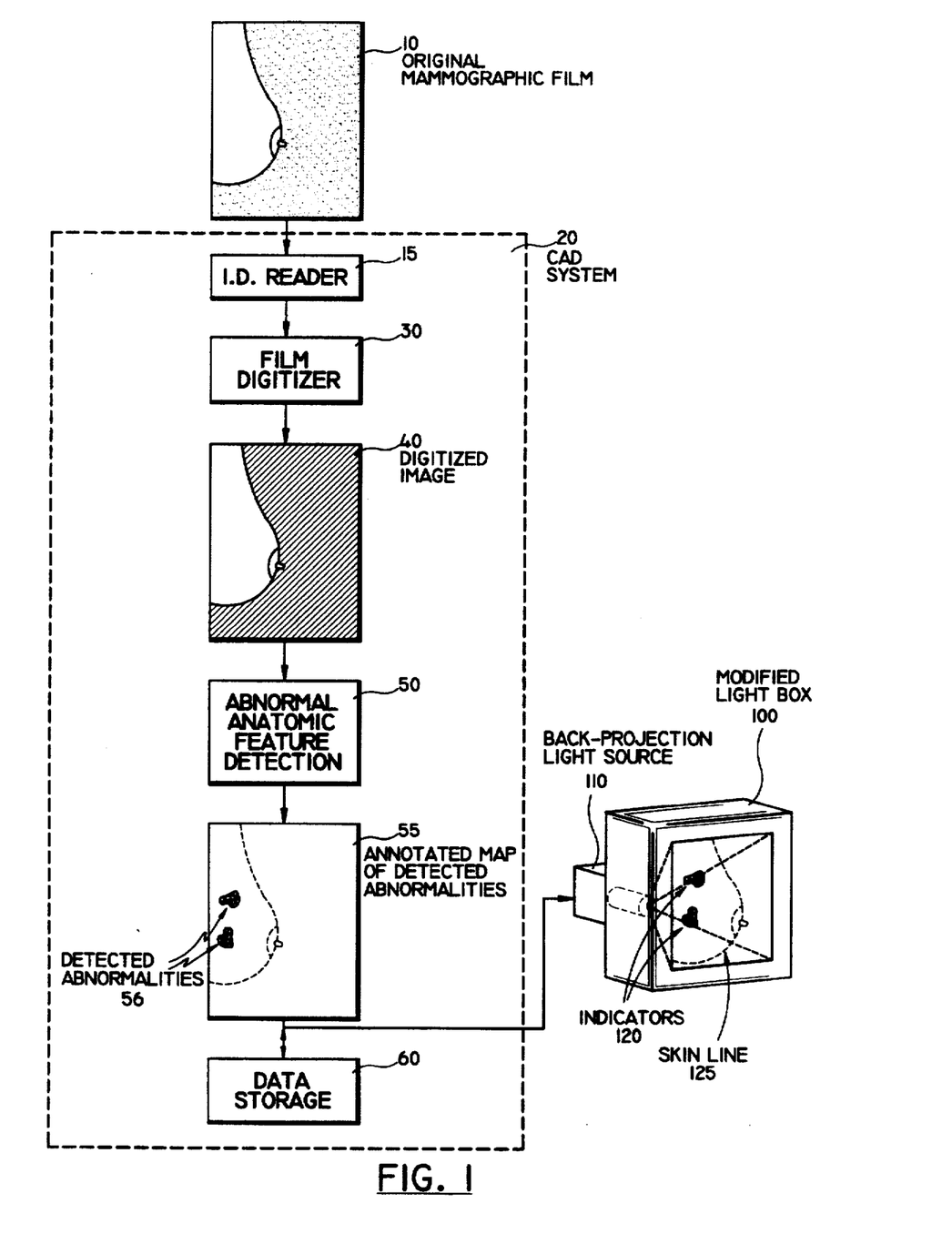
FIG. 1 is a schematic diagram illustrating a CAD system and its output display according to the first embodiment of the invention.

Referring to FIG. 1, a preferred but non-limiting example of the invention generates an annotation map of CAD-detected abnormalities and selectively displays it in registration with an x-ray film. In this example, the radiologic image is in the form of a mammographic x-ray film, which is acquired with a conventional mammographic film-screen imaging system. The original analog two-dimensional mammographic x-ray film 10 is first sent through the film digitizer 30 of a CAD (computer-aided diagnosis) machine 20 (such as that disclosed in the documents which are incorporated by reference herein) to obtain a digitized two-dimensional mammographic image 40. Preferably, the film digitizer 30 should be a laser film digitizer and should have a dynamic range and a spatial resolution comparable to those of the original mammographic film which typically has a dynamic range of 10,000:1 and spatial resolution of approximately 50 microns per pixel (or about 4,000×5000 pixels per image). The identity of the original mammographic image 10 is also entered into the CAD system at this point to identify the digitized mammographic image 40. An useful option at this point is to automatically input the identity of this original mammographic image 10 into the CAD machine. This can be accomplished, for example, by first labeling the mammographic film 10 with a code such as a bar code, and then by reading the label into the CAD system 20 with an optional ID bar code reader 15 as the mammographic film 10 is being fed into the film digitizer 30.

Certain radiologic images may already be in the digital format, such as images that were acquired with a digital imaging system in the form of a computed tomography system, an ultrasound imaging system, a scintillation camera, a digital stimulated emission phosphor plate radiography system such as Fuji's Computed Radiography or recently reported digital mammographic systems using CCDs, MRI systems, or some other digital imaging system. Such digitized images can be directly entered in the CAD system 20 as the digitized image 40 and the initial film digitization step is not needed in this case.

The digitized mammographic image 40 is then sent through the abnormal feature detection stage 50 of the CAD machine 20. The findings or results, positive or negative in nature, from abnormal feature detection stage 50 are in the form of a two-dimensional annotation map 55, or x-y coordinate information, of the locations of the CAD-detected abnormalities 56 from the original film image 10. The CAD-generated annotation map 55 may be stored for later use in an optional memory storage unit 60, together with the digitized image 40 and its corresponding identification. This annotation map 55 is then transferred to the output display section of the system for display. The output display section of the CAD system may be a part of the total CAD system, and in which case the data transfer can be through a dedicated shielded cable. The output display section may also be a separate system, and in which case an additional data storage memory may be added to the unit to store the transferred interim data and the data transfer may be conducted through a dedicated shielded cable or an existing network where the equipment is installed.

As shown in FIG. 1, displaying the annotation map 55 involves scaling the annotation map 55 to the same size as the original film image 10 (which scaling can be carried out in box 100), and displaying the so-scaled annotation map 55 on a modified light box 100 using a back-projected high intensity light source 110. The back-projected high intensity light source 110 projects the annotation map 55 with indicators 120 in the form of, e.g., cursor arrows) marking the location of the detected abnormalities 56. The original film image 10 can be placed over the modified light box 100, in registration with the scaled annotation map 55, so that the radiologist can view the x-ray film image 10 and the annotation map 55 as a single composite image, or can turn off the display of the annotation map 55 and selectively view only the x-ray image on the modified light box 100. Additional registration or alignment aids, for example for mammography applications, in the form of outlines of the skin line 125 of the imaged breast, may also be a part of the annotation map. The breast border or breast skin line 125 is typically sufficiently unique to the imaged breast, and as an alignment aid it not only helps in the alignment but also provides confidence to the radiologist that the he or she is looking at the mammogram with the correct annotation map.

Figure 2:
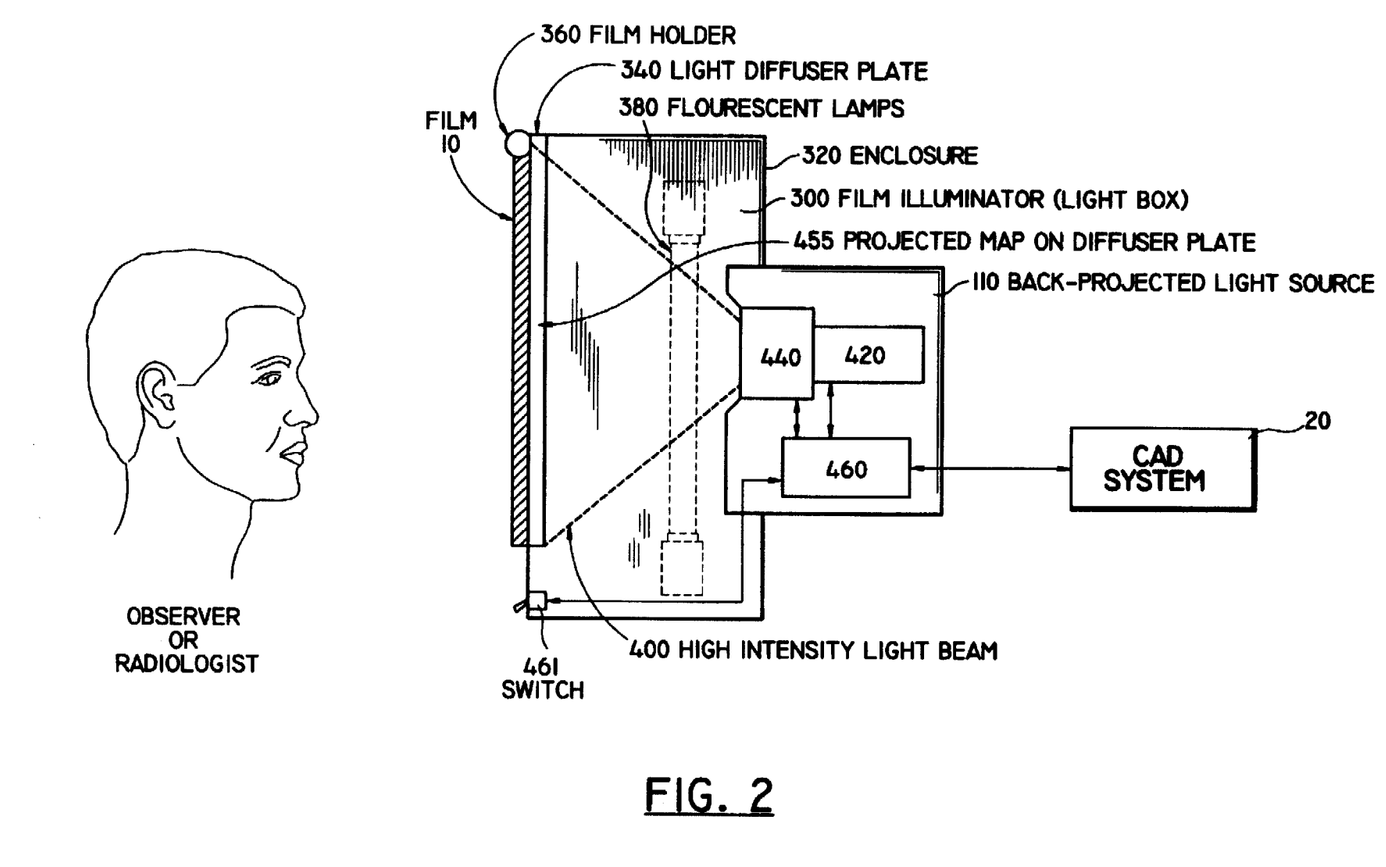
FIG. 2 is a schematic diagram illustrates the side view of a CAD output display comprising of a conventional film illuminator and a back-projecting high intensity scanning light source, such as a scanning laser beam, according to the first embodiment of the invention.

Referring to FIG. 2, the modified light box 100 is made of two components: a conventional high brightness film illuminating light box 300 and a back-projected high intensity light source 110.

The light box 300 has an enclosure 320, a translucent plastic light diffuser plate 340 as the front window, a film holder 360 on the top edge of the film illuminator 300, and a light source in the form of fluorescent lamps 380.

The back-projected high intensity light source 110 has a high intensity light beam 400 provided by the high intensity light source 420, a scanning device 440 to project the light beam 400 onto the back surface of the light diffuser plate 340, and a controller device 460 which translates the annotation map 5B from the CAD system 20 into a properly scaled annotation map 455 projected on the back surface of the light diffuser plate 340. As also shown in FIG. 2, the original film 10 is mounted on the light box 300, in the conventional manner, on the front surface of the light diffuser plate 340 for viewing by the observer or the radiologist. The image of the projected annotation map 455 can be toggled on and off with the back projector 110 by manually operating a switch 461 attached to the controller device 460. The high intensity light source 420 can be a high intensity diode laser device with sufficient brightness and color to attract the observer's attention as the observer is viewing the original image 10. Depending on the scanning method, raster scan or vector scan, and the color and duration or length of time of the light beam 400 stays at a given indicator 120 during the display, the required light beam power may vary in the range of several milliwatts to several watts. The scanning device 440 may provide a raster scan or a vector scan. The spatial resolution may be comparable to or less than that of current NTSC or PAL broadcast television. This scanning device 440 may be a mechanical gimbal or a set of two orthogonally oriented moving mirrors or an array of modulatable mirrors on a silicon chip. In the case of a vector scan configuration, the system design may be quite straightforward. The light source 420 may be a low power diode laser and the scanning device 440 may be constructed from scanning mirrors manufactured by Cambridge Technology, Inc. or by General Scanning Inc. Both companies are located in Watertown, Mass. In the vector scan configuration, the light beam 400 is repeatedly directed to display the annotation map only, i.e. the indicators 120 and the breast border or skin line 125, and the light beam spends more time on the annotation map than would be in the case of raster scan. The required light beam power is also reduced.

Using the CAD system as a second reader or a prompting device, the radiologist can first review the original film 10 on the modified light box 100, without at that time displaying the annotation map 55, and can make a preliminary diagnostic decision. During this first viewing, the modified light box 100 simply operates as a film illuminator and no indicators such as 120 are displayed. Then, without moving the original film 10 from the modified light box 100, the radiologist can activate switch 461 to turn on the display of the back-projected annotation map 455, thereby displaying indicators 120 to mark the CAD-detected abnormalities for the same original film 10. After viewing the original film 10 with the detected abnormalities marked by indicators 120, the radiologist can make the final diagnostic decision, which may or may not be same as the preliminary decision and can be influenced by additional diagnostic information provided by the CAD-detected abnormalities. The radiologist can go back and forth between the annotated and non-annotated images, without taking his or her eyes off the x-ray film, simply by toggling switch 461 to turn on and off the display of annotation map 455.

Figure 3:
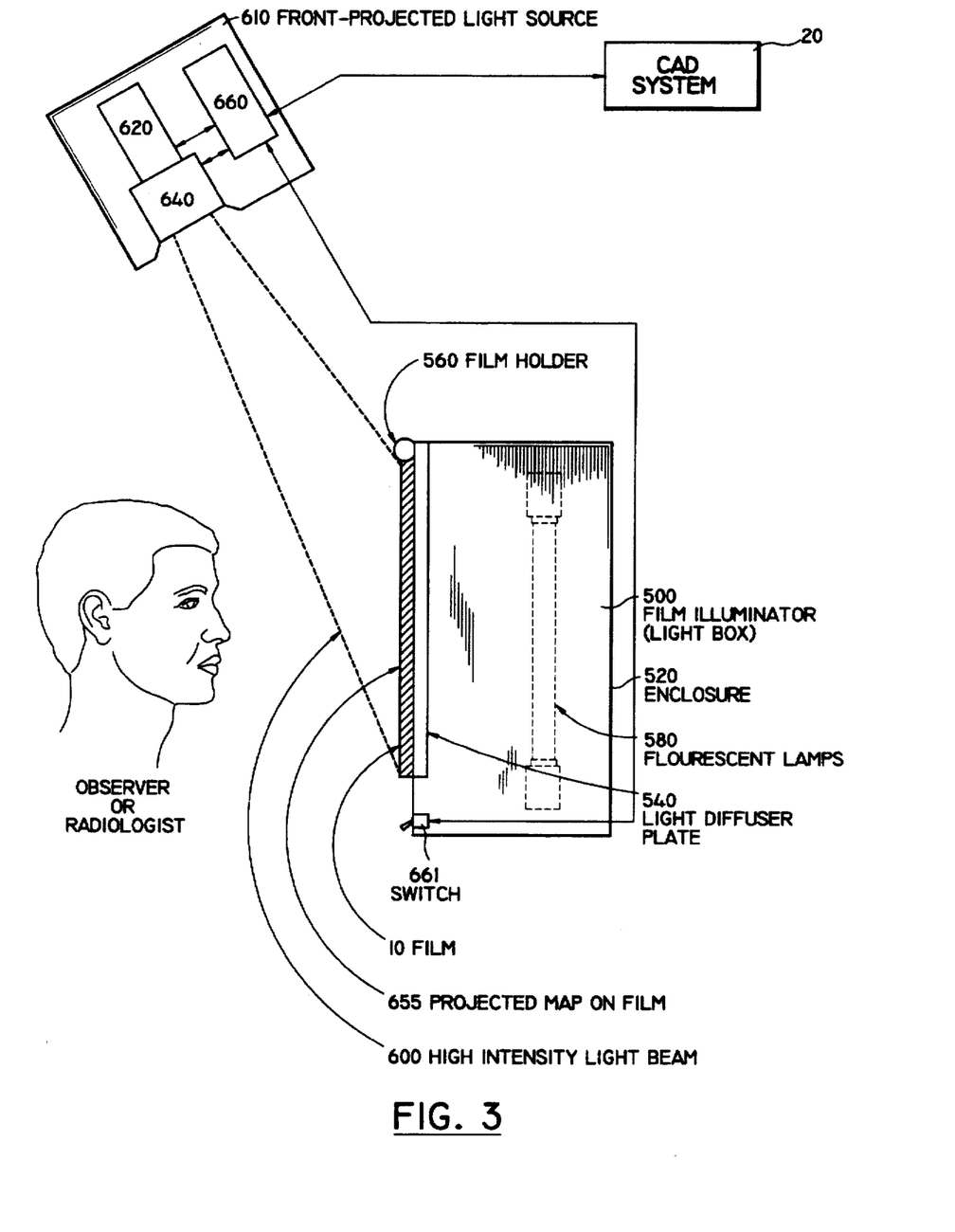
FIG. 3 is a schematic diagram illustrates the details of a CAD output display comprising of a conventional film illuminator and a front-projecting high intensity scanning light source, such as a scanning laser beam, according to the second embodiment of the invention.

The second embodiment of the invention is illustrated in FIG. 3 (a schematic side view). This embodiment is yet another arrangement to annotate the original film 10—by replacing the back-projected high intensity light source 110 of the first embodiment with a front-projected high intensity light source 610, located external to the light box 500.

This light box 500 has an enclosure 520, a translucent plastic light diffuser plate 540 as the front window, a film holder 560 on the top edge of the film illuminator 500, and a light source in the form of fluorescent lamps 580.

The front-projected high intensity light source 610 has a high intensity light beam 600 provided by the high intensity light source 620, a scanning device 640 to project the light beam 600 onto the front surface of the light box's light diffuser plate 540, and a controller device 660 which translates the annotation map 55 from the CAD system 20 into a properly scaled annotation map 655 projected on the front surface of the light diffuser plate 540. As also shown in FIG. 3, the original film 10 is mounted on the light box 500, in the conventional manner, on the front surface of the light diffuser plate 540 for viewing by the observer or the radiologist. The image of the projected annotation map 655, after the original film 10 is mounted, is thus projected directly on the original film 10. The projected annotation map 655 can be toggled on and off by manually operating a switch 661 attached to the controller device 660. The high intensity light source 620 can be a high intensity diode laser device with sufficient brightness and color to attract the observer's attention as the observer is viewing the original image 10. Depending on the scanning method, raster scan or vector scan, and the color and duration or length of time of the light beam 600 stays at a given indicator 120 during the display, the required light beam power may vary in the range of several milliwatts to several watts. Again, the scanning device 640 may provide a raster scan or a vector scan. The spatial resolution may be comparable to or less than that of current NTSC or PAL. This scanning device 640 may be a mechanical gimbal or a set of two orthogonally oriented moving mirrors or an array of modulatable mirrors on a silicon chip. In the case of a vector scan configuration, the system design may be quite straightforward. The light source 620 may be a low power diode laser and the scanning device 640 may be constructed from scanning mirrors manufactured by Cambridge Technology, Inc. or by General Scanning Inc. Both companies are located in Watertown, Mass. In the vector scan configuration, the light beam 600 is repeatedly directed to display the annotation map only, i.e. the indicators 120 and the breast border or skin line 125, and the light beam spend more time on the annotation map than would be in the case of raster scan. The required light beam power is also reduced. The front-projected approach also requires less light beam power than the back-projected approach, because the front-projected light beam does not have to transmit through the original film 10 in order to attract the observer's attention. A possible drawback of the front-projected approach is that it may sometimes get in the way of the observer.

Figure 4:
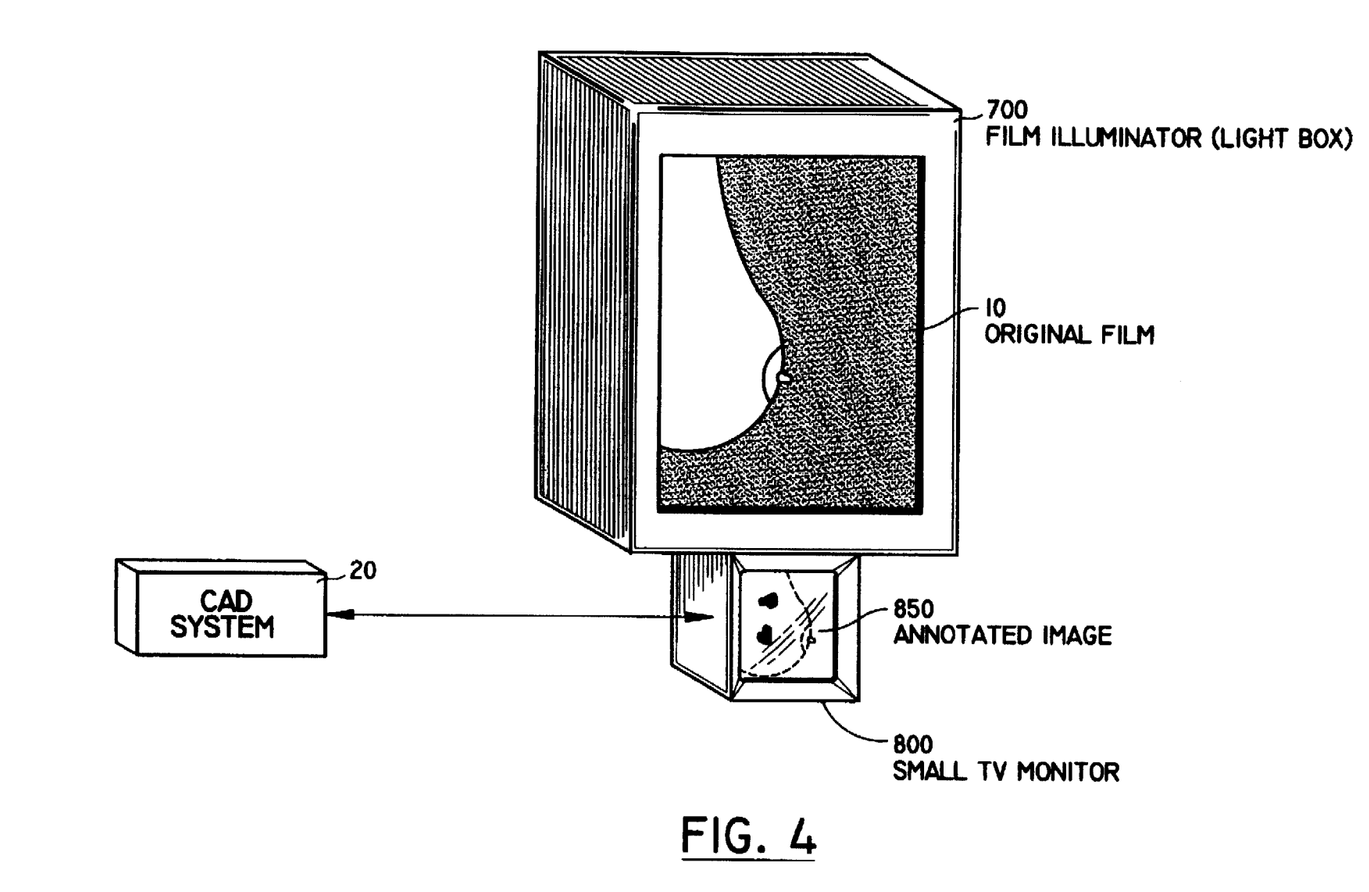
FIG. 4 is a schematic diagram illustrates a CAD output display comprising of a conventional film illuminator and small road map TV monitor according to the third embodiment of the invention.

FIG. 4 is a schematic diagram illustrates a CAD output display comprising of a conventional film illuminator 700 and a small, road map TV monitor 800 according to the third embodiment of the invention. In this exemplary embodiment, the annotated information is presented as a miniaturized annotation road map image 850 on a small TV monitor 800, located in close proximity to the original film 10. This miniaturized road map image 850 is made of two superimposed images: a subsampled image generated from the digitized image 40 and a likewise subsampled image generated from the corresponding annotation map 55. The ratio of the size, as measured by the length of the diagonal of the image, of the original film 10 to the miniaturized annotated road map image 850, can be in the order of 2:1 to 4:1. The center of the small TV monitor 800 typically is less than 12 inches from the center of the original film 10 on the conventional film illumination light box 700. The preferred position, as shown in FIG. 4, for mounting the small TV monitor 800 is just beneath the light box 700 which displays the original image 10. It is also convenient to display a pair of images on each monitor, since frequently a pair of the original films 10 are displayed and viewed next to each other. In this manner, the radiologist still has to move his or her eyes back and forth between the original radiologic film image 10 on the film illuminator 700 and the miniaturized annotated road map 850 displayed on the small TV monitor 800. The spatial resolution of the small TV monitor 800 can be in the range of 500 TV lines, or comparable to that of current NTSC or PAL. The brightness level of the small TV monitor 800 should be similar to that of the average brightness transmitted through the original film 10, so that the observer would not be bothered by a brightness change from one image to the other. It is also important that the miniaturized annotated road map image 850 can be easily toggled on-off with a switch (not shown) by the observer. While diagnostic errors could arise from the back and forth movement of he observer's eyes, the much shorter distance and the much smaller angle subtended by the eye between the annotated road map and the original film image as compared to the system described by Giger et al. in Proceedings of SPIE, Volume 1445 (1991), pages 101–103, is expected be able to minimize the anticipated errors. The TV monitor 800 can be at a different convenient position, e.g. to the side or above light box 700.

Although the embodiments above has been described in terms of preferred structures involving a single original film, it should be apparent to those skilled in the art that this invention also applies to viewing of multiple films on a multiple-film viewing station or an alternator (a multiviewer having pre-loaded films and a transport belt) can allow several x-ray films 10 to be viewed at the same time or different times, with or without their respective annotation maps 55.

Although the invention has been described in terms of preferred structures and processes, it should be apparent to those skilled in the art that various alterations and modifications can be made without departing from the invention and that such modification and a alterations are intended to be considered to be within the spirit and scope of the invention as defined by the appended claims.

I claim:

1. A system comprising:
    a source of digitized image data representing x-ray film characterized by high spatial resolution;
    a processor coupled with said source to receive said digitized image data, to process said data to detect abnormal anatomical features meeting selected criteria, and to generate lower resolution annotation maps identifying image portions meeting said selected criteria; and
    a display coupled with said processor and displaying said x-ray film for viewing at full analog spatial and contrast resolution and at a high brightness level while selectively superposing thereon said annotation maps in registration therewith;
    wherein, said x-ray film is annotated with a scanning high intensity light beam.

2. A system as in claim 1 in which said source comprises a digitizer processing said x-ray film to provide said digitized image data.

3. A system as in claim 2 in which said scanning high intensity light beam is projected from behind said x-ray film during the viewing of said x-ray film.

4. A system as in claim 2 in which said scanning high intensity light beam is projected from the front of said x-ray film during the viewing of said x-ray film.

5. A system as in claim 1 in which said scanning high intensity light beam is projected from a diode laser.

6. A system as in claim 1 in which said display comprises an x-ray film light box selectively illuminating for viewing x-ray films placed thereon and an annotation map source co-acting with said light box to selectively display said lower resolution annotation maps in superposition on and registration with the x-ray films being viewed.

7. A system comprising:
    a source of digitized image data representing an x-ray film image characterized by high spatial resolution;
    a processor coupled with said source to receive said digitized image data, to process said data to detect abnormal anatomical features meeting selected criteria, and to generate an annotation map identifying image portions corresponding to said abnormal anatomical features;
    a main display showing said x-ray film image for viewing at said high spatial resolution; and
    a supplemental display positioned in close proximity to said main display and showing a reduced spatial resolution version of said x-ray film image and further selectively showing a matching version of said annotation map in registration therewith.

8. A system as in claim 7 in which said annotation map comprises markers indicative of abnormalities which meet a selected probability threshold.

9. A system as in claim 7 in which said annotation map comprises a different marker for each different type of a selected set of abnormalities.

10. A system as in claim 7 including a printer printing said annotation map and said reduced spatial resolution version x-ray film image to provide a hard copy printed record thereof.

11. A system as in claim 7 wherein said processor selectively processes said digitized image data to image-enhance one or more of said selected image portions.

12. A system as in claim 7 including a printer printing said annotation map and said reduced spatial resolution version x-ray film image in superposition and registration therewith to provide a hard copy printed record thereof.

13. A system as in claim 12 in which said annotation map comprises markers indicative of abnormalities which meet a selected probability threshold.

14. A system as in claim 13 in which said annotation map comprises markers indicative of abnormalities which meet a selected probability threshold.

15. A system as in claim 14 wherein said processor selectively processes said digitized image data to image-enhance one or more of said selected image portions.

16. A system as in claim 7 wherein said annotation map comprises markers indicative of abnormalities which meet a selected probability threshold, and said processor selectively processes said digitized image data to image-enhance one or more of said selected image portions.

17. A system as in claim 7 wherein said processor selectively processes said digitized image data to image-enhance one or more of said selected image portions, and including a printer printing said annotation map and said reduced spatial resolution version x-ray film image in superposition and registration therewith to provide a hard copy printed record thereof.

18. A system as in claim 7 wherein said annotation map comprises a different marker for each different type of a selected set of abnormalities, and said processor selectively processes said digitized image data to image-enhance one or more of said selected image portions.

19. A method comprising:
    providing digitized image data representing an x-ray film image, said image data being characterized by relatively high spatial resolution;
    computer-processing said digitized image data to detect abnormal anatomical features;
    generating an annotation map identifying image portions corresponding to said abnormal anatomical features;
    displaying said x-ray film image on a light box at a relatively high spatial resolution for viewing at a main display;
    displaying said x-ray film image at a reduced size and a relatively low spatial resolution at a supplemental display positioned below said light box so that a viewer can conveniently view both supplemental and main displays;
    displaying at said supplemental display said annotation map in registration with said reduced size x-ray film image displayed at said supplemental display.

20. A method as in claim 19 including printing a hard copy of said annotation map.

21. A method as in claim 19 including printing a hard copy of said reduced size x-ray image and said annotation map superimposed thereon.

22. A method as in claim 19 in which said computer-processing comprises detecting abnormal anatomical features which meet a selected probability threshold.

23. A method as in claim 19 in which said generating comprises generating an annotation map having a different marker for each different type of a selected set of abnormal anatomical features.

24. A method as in claim 19 including selectively processing said digitized image data to image-enhance portions thereof corresponding to one or more of said abnormal anatomical features.

25. A method as in claim 7 wherein said generating comprises generating an annotation map comprising markers indicative of abnormal anatomical features which meet a selected probability threshold, and including selectively processing said digitized image data to image-enhance one or more selected image portions thereof.

26. A method as in claim 19 including selectively processing said digitized image data to image-enhance one or more selected image portions, and printing said annotation map and said reduced spatial resolution version x-ray film image in superposition and registration therewith to provide a hard copy printed record thereof.

27. A method as in claim 19 in which said generating comprises generating an annotation map comprising a different marker for each different type of a selected set of said abnormal anatomical features, and including selectively processing said digitized image data to image-enhance one or more selected image portions.

28. A method as in claim 19 including positioning said monitor is within 12 inches of said light box.

29. A method as in claim 19 in which the ratio of the diagonals of the x-ray film displayed at said light box and the display at said monitor is in the range of 2:1 to 4:1.

* * * * *